US012465715B2

(12) United States Patent
Xu et al.

(10) Patent No.: US 12,465,715 B2
(45) Date of Patent: Nov. 11, 2025

(54) NOISE REDUCTION DEVICE FOR RESPIRATORY APPARATUS

(71) Applicants: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

(72) Inventors: Jiebing Xu, Guangdong (CN); Haibin Yu, Guangdong (CN); Zhenxiang Hu, Guangdong (CN); Yu Lei, Guangdong (CN)

(73) Assignees: VINCENT MEDICAL (DONG GUAN) MANUFACTURING CO., LTD., Guangdong (CN); VINCENT MEDICAL (DONGGUAN) TECHNOLOGY CO., LTD., Guangdong (CN)

( * ) Notice: Subject to any disclaimer, the term of this patent is extended or adjusted under 35 U.S.C. 154(b) by 925 days.

(21) Appl. No.: 17/437,113

(22) PCT Filed: Jun. 6, 2019

(86) PCT No.: PCT/CN2019/090387

§ 371 (c)(1),
(2) Date: Sep. 8, 2021

(87) PCT Pub. No.: WO2020/243956

PCT Pub. Date: Dec. 10, 2020

(65) Prior Publication Data

US 2022/0176061 A1 Jun. 9, 2022

(51) Int. Cl.

| | |
|---|---|
| ***A61M 16/10*** | (2006.01) |
| ***A61M 16/12*** | (2006.01) |
| ***A61M 16/16*** | (2006.01) |

(52) U.S. Cl.

CPC ........ *A61M 16/107* (2014.02); *A61M 16/125* (2014.02); *A61M 16/16* (2013.01); *A61M 2205/42* (2013.01)

(58) Field of Classification Search

CPC ................ A61M 2205/42; A61M 16/105–107
See application file for complete search history.

(56) References Cited

U.S. PATENT DOCUMENTS

| | | | | |
|---|---|---|---|---|
| 11,247,007 B2 * | 2/2022 | Nitta | .................. | A61M 16/022 |
| 11,505,171 B2 * | 11/2022 | Sovago | ................ | F15B 21/008 |

(Continued)

FOREIGN PATENT DOCUMENTS

| | | | |
|---|---|---|---|
| CN | 101075431 A | | 11/2007 |
| CN | 100587804 C | * | 2/2010 |

(Continued)

OTHER PUBLICATIONS

International Search Report and Written Opinion of the International Searching Authority issued for International PCT Application No. PCT/CN2019/090387 on Feb. 26, 2020.

(Continued)

*Primary Examiner* — Joseph D. Boecker
*Assistant Examiner* — Thomas W Greig
(74) *Attorney, Agent, or Firm* — Howson & Howson LLP

(57) ABSTRACT

A noise reduction device for a respiratory apparatus including a body with a gas outlet arranged to be mounted on the gas inlet of the respiratory apparatus, and a cover configured to be detachably engaged with the body for forming a gas inlet and a gas passage. The cover includes a guiding member to define at least a part of the gas passage and the guiding member is configured to be coupled with the body to form the gas passage between the body and the cover. The noise reduction device provides a longer and smooth passage for the gas to flow from the gas inlet to the gas outlet (Continued)

for reduction of turbulence and resistance of gas flow and hence reducing the noise caused by the friction between the fluctuated gas flow and the gas inlet of the respiratory apparatus.

17 Claims, 5 Drawing Sheets

(56) References Cited

U.S. PATENT DOCUMENTS

| | | | | |
|---|---|---|---|---|
| 2004/0231913 | A1* | 11/2004 | McCombs | F01N 1/24 181/258 |
| 2007/0169781 | A1* | 7/2007 | Tang | A61M 16/00 128/205.25 |
| 2008/0127976 | A1* | 6/2008 | Acker | A61M 16/08 128/204.18 |
| 2008/0257346 | A1* | 10/2008 | Lathrop | A61M 16/0066 181/224 |
| 2010/0000535 | A1* | 1/2010 | Wickham | A61M 16/20 128/205.24 |
| 2010/0054969 | A1* | 3/2010 | Grasmuck | F04D 29/5806 415/206 |
| 2010/0132708 | A1* | 6/2010 | Martin | A61M 16/0066 128/204.21 |
| 2012/0037160 | A1 | 2/2012 | Sung | |
| 2014/0299406 | A1* | 10/2014 | Librett | A61M 16/0858 181/224 |
| 2015/0023782 | A1* | 1/2015 | Velzy | A61M 16/0066 415/119 |
| 2015/0273167 | A1 | 10/2015 | Feldhahn et al. | |

FOREIGN PATENT DOCUMENTS

| | | | |
|---|---|---|---|
| CN | 202105279 | U | 1/2012 |
| CN | 204025176 | U | 12/2014 |
| CN | 206613010 | U | * 11/2017 |
| CN | 207323803 | U | 5/2018 |
| JP | 2001-278604 | A | 10/2001 |

OTHER PUBLICATIONS

Office Action dated Dec. 8, 2022 issued by the Japanese Patent Office for corresponding Japanese Patent Application No. 2021-564102.

European Search Report for corresponding EP Application No. 19932111.8, Mar. 15, 2023.

* cited by examiner

NOISE REDUCTION DEVICE FOR RESPIRATORY APPARATUS

CROSS-REFERENCE TO RELATED APPLICATION(S)

This is a national stage application filed under 37 U.S.C. 371 based on International Patent Application No. PCT/CN2019/090387, filed Jun. 6, 2019, the disclosures of which is incorporated herein by reference in its entirety.

TECHNICAL FIELD

The present invention relates to a noise reduction device for a respiratory apparatus, particularly, for noise reduction at a gas inlet of the respiratory apparatus.

BACKGROUND OF THE INVENTION

In modern clinical medicine, a respiratory apparatus is commonly used for patients with respiratory illnesses such as acute respiratory distress syndrome, severe asthma and chronic obstructive pulmonary disease, as well as used for anesthesia and respiratory management during surgery, first aid resuscitation, and even domestic use for supportive treatment. A respiratory apparatus is a vital medical device that can prevent and treat respiratory failure, reduce complications and prolong the patient's life.

Current respiratory apparatuses have a number of drawbacks. For example, when air is drawn into a respiratory apparatus by a blower, noise is generated by the friction between the air flow and the gas inlet passage. The noise is particularly obvious when the respiratory apparatus is used in a quiet environment or when the patient is sleeping, potentially causing a physical and mental annoyance to the patient.

There are many designs of a noise reduction device to reduce the noise generated at the gas inlet of the respiratory apparatus. For example, CN101075431A to Hongqing Wang, published on 21 Nov. 2007, discloses a noise reduction device including a gas passage defined by a side wall to direct gas flow into the respiratory apparatus. The gas may only travel an angular distance of 60 degrees before reaching the gas outlet, which is too short for the gas passage to reduce the turbulent gas flow and thus provide an effective noise reduction. Accordingly, it has been found that such a design cannot provide significant noise reduction.

It is therefore desirable to provide an improved noise reduction device for the gas to flow from the gas inlet to the gas outlet in order to reduce noise level at the gas inlet of a respiratory apparatus significantly.

SUMMARY OF THE INVENTION

The present invention provides a noise reduction device for a respiratory apparatus to, at least, solve the technical problem of the noise generated by/at the gas inlet of the current respiratory apparatus.

According to an aspect of the present invention, there is provided a noise reduction device for a respiratory apparatus including a body configured to be mounted on the gas inlet of the respiratory apparatus, and a cover configured to be detachably engageable with the body for forming a gas inlet and a gas passage. The body includes a side wall and a gas outlet and the cover includes a guiding member defining at least a part of the gas passage. The guiding member is configured to be coupled with the side wall of the body to form the gas passage between the body and the cover.

According to another aspect of the invention, there is provided a respiratory apparatus including the noise reduction device substantially as described herein. The respiratory apparatus may further include a pressurized gas inlet for supplying a pressurized gas; a chamber in fluid communication with the gas outlet of the noise reduction device and the pressurized gas inlet for mixing atmospheric air and the pressurized gas; and a noise-damping device disposed downstream of the chamber.

Without intending to be limited by theory, it is believed that the noise reduction device in the present invention provides significant advantages over, for example, current noise reduction devices that only allow a gas flow to turn about 60 degrees relative to the gas inlet before discharging at the gas outlet. Specifically, it is believed that the noise reduction device in the present invention may provide a longer path, and in an embodiment herein, a longer spiral passage for the gas to flow from the gas inlet to the gas outlet so as to decrease the turbulence and resistance of gas flow to a larger extent and hence reducing the noise caused by the friction between the turbulent gas flow and the gas inlet of the respiratory apparatus. Moreover, it is believed that the configuration of the guiding member being located on the cover provides an easier and more convenient way to clean the gas passage. The cover can be disengaged from the body and subject to common sterilization methods of medical equipment. Such arrangement may also facilitate replacement of the cover in case abrasion or damage is found on the guiding member which may increase turbulent flow of the incoming gas and thus causes noise.

The figures herein are for illustrative purposes only and are not necessarily drawn to scale.

DETAILED DESCRIPTION OF THE INVENTION

The present invention relates to a noise reduction device which is useful to minimize the noise generated when a gas, in particular atmospheric air or pressurized gas, enters the associated apparatus such as, but is not limited to, a respiratory apparatus which requires a supply of a gas. The respiratory apparatus may be, but is not limited to, a humidifier, a respirator, a nebulizer, etc.

The gas useful herein typically includes atmospheric air or air enriched with oxygen gas, as desired. The gas herein may be at ambient room temperature, higher than room temperature, or lower that room temperature, as desired. The gas herein may be at the ambient pressure of the surrounding environment, or at a higher pressure than the surrounding environment. The gas herein may be at ambient humidity, more humid than ambient humidity, or drier than ambient humidity, as desired.

Figure 1:
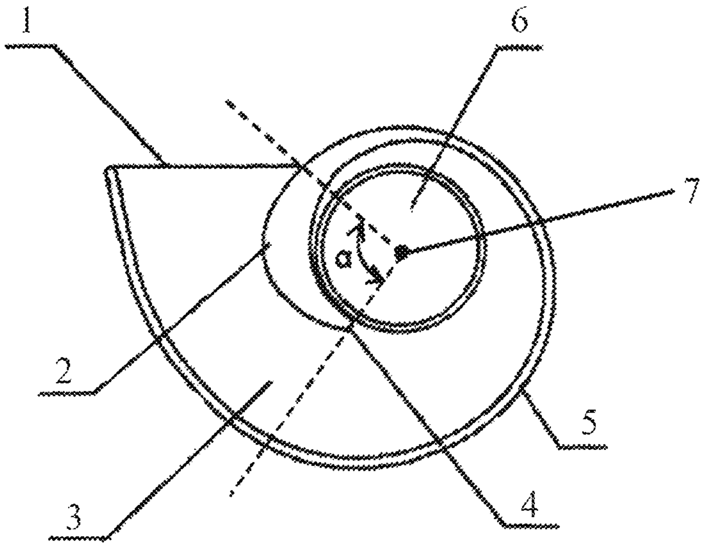
Figure 1 PRIOR ART
FIG. 1 shows a noise reduction device in the reference CN101075431A (see above)

FIG. 1 shows a noise reduction device disclosed in, for example, CN101075431A (see above). The noise reduction device includes a gas passage 3 defined by a side wall 5. A gas inlet 1 is provided at outer end of the gas passage 3 and a gas outlet 6 with a centre 7 is provided at the inner end of the gas passage 3. Two dashed lines are added to FIG. 1, with one extending from the centre 7 to the gas inlet 1 and one extending from the centre 7 to an inner end 4 of the side wall 5, to define an angular rotation a about the centre 7 to show the shortest distance for the incoming gas to travel from the gas inlet 1 to the gas outlet 6, which is about 90 degrees. In other words, gas may only travel about 90 degrees before reaching the gas outlet, which is too short for the gas passage to reduce the turbulent gas flow and thus provide an effective noise reduction. Accordingly, it has been found that such a design cannot provide significant noise reduction.

Figure 2:
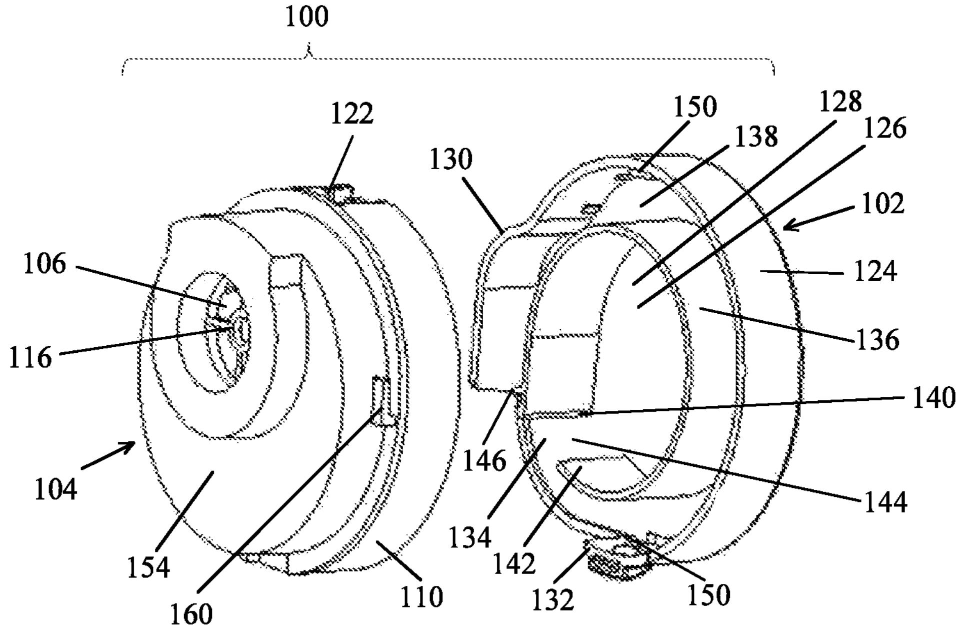
FIG. 2 shows a perspective view of an embodiment of the noise reduction device herein when the body and the cover are disengaged from each other.

Referring to FIG. 2, there is illustrated an embodiment of a noise reduction device of the present invention. The noise reduction device 100 of the present invention has a cover 102 and a body 104. The cover 102 and the body 104 are, preferably, separately manufactured and can be detachably engaged with each other through a locking means such as sliding and screwing.

In this embodiment, the cover 102 and the body 104 may be made of a plastic, such as a thermoset plastic, a resin, a polymeric material, etc. Such plastics are known in the art and typically include materials such as polycarbonate, polyethylene, polypropylene, polyvinyl chloride, acrylonitrile butadiene styrene, polymethyl methacrylate, phenolics, melamine formaldehyde, polysulfone, polyetherimide, polyethylene terephthalate, urea-formaldehyde, polyether ether ketone, and a combination thereof. Furthermore, the plastic may incorporate an anti-microbial compound by, for example, containing a coating, integrating the anti-microbial compound into the plastic, etc.

Figure 3:
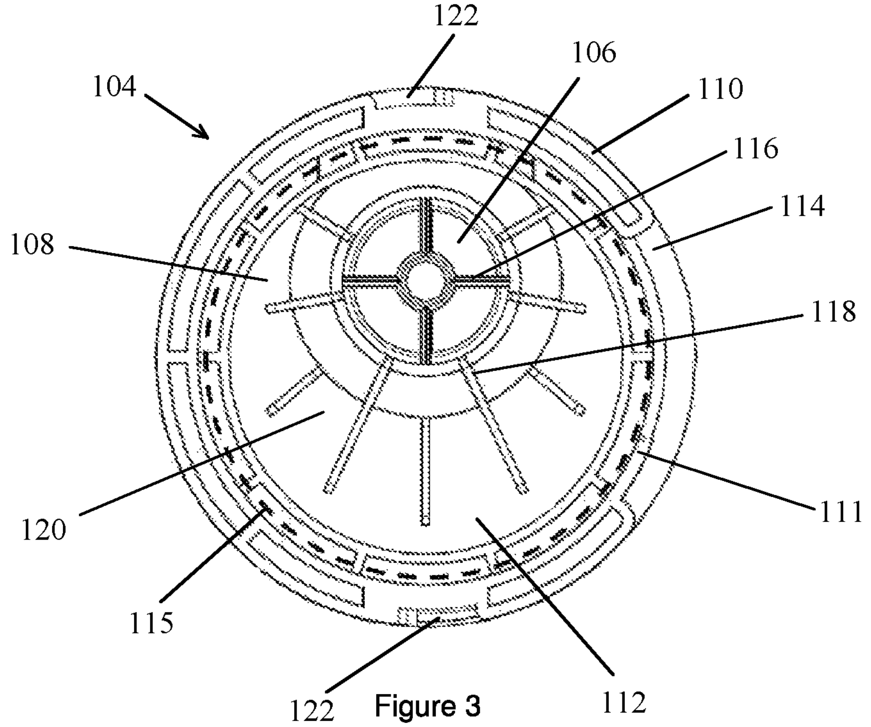
FIG. 3 shows a front view of an embodiment of the body before engaging with the cover.

FIG. 3 shows an embodiment of the body 104 before engaging with the cover (see FIG. 2 at 102). The body 104 has a gas outlet 106 and is preferably arranged to be mounted to a respiratory apparatus (see FIG. 7 at 162) so as to discharge a gas into the respiratory apparatus for subsequent use. In this embodiment, the body 104 is configured with a cavity 108 surrounded by a side wall 110. The side wall 110 extends perpendicularly from periphery of an inner surface 112 and includes a first end portion 111. The cavity 108 may be open or closed depending on the configuration of the side wall 110. In this embodiment, the cavity 108 is open with the side wall 110 configured as a C-shape, i.e. leaving an open portion 114. At least part of the side wall 110 can be coupled to the cover (see FIG. 2 at 102) for forming a tight seal.

The cavity 108 may house a filter 115 (shown as a dotted line) therein. The filter 115 may be provided to filter dust, pollen, mold, bacteria, etc. from the gas, particularly atmospheric air, before the gas enters the respiratory apparatus. In an embodiment where the filter 115 is detachably arranged in the cavity 108 of the body 104, the filter 115 can be replaced with a new one either randomly or regularly so as to keep the filtered gas free from, or at least with a reduced amount of, dust, pollen, mold, bacteria, etc. This is particularly advantageous when the respiratory apparatus is used for clinical applications. It is also believed that the filter 115 can also act as a noise suppressor to reduce the noise generated in the cavity 108 when the gas passes through the noise reduction device (see FIG. 2 at 100). The filter 115 may be, for example, a paper filter, foam filter, cotton filter, or high-efficiency particulate air filter. One skilled in the art would appreciate that various suitable filters can be applied to the noise reduction device 100 of the present invention.

In this embodiment, the gas outlet 106 is radially offset and is supported by a supporting structure 116 which has a plurality of upright protrusions 118 on the inner surface 112 connecting to the gas outlet 106. The gas outlet 106 may be aligned with the gas pathway in the respiratory apparatus, thereby reducing the formation of turbulence. One skilled in the art would appreciate that the gas outlet 106 may be positioned at the centre of the cavity 108 to achieve the similar purpose.

The cavity 108 may further include a converging portion 120 on the inner surface 112 which converges towards the gas outlet 106 so as to facilitate the gas flow. In addition to guiding the flow of the gas towards the gas outlet 106, the supporting structure 116 may also help to hold the filter 115 in place. Without intending to be limited by theory, it is also believed that the upright protrusions 118 and supporting structure 116 may further enhance the structural integrity of the body 104 and/or the cover (see FIG. 2 at 102). The upright protrusions 118 and the converging portion 120 support the filter 115 which may help to separate the filter 115 from the inner surface 112 to increase the effective surface area of the filter 115 and hence increase the amount of filtered gas flow. This may synergistically help to protect a blower of the respiratory apparatus (see FIG. 7 at 162) by reducing its workload and thus further reducing the noise produced. In this embodiment, the upright protrusions 118 of the supporting structure 116 are configured as extending, continuously or discontinuously, radially from the gas outlet 106.

In the embodiment of FIGS. 2 and 3, the body 104 is configured to detachably engage with the cover 102. Preferably, the body 104 is enclosed by the cover 102 after engaging with the cover 102. The body 104 may include two slots 122 (or tabs) respectively arranged on substantially diametrically opposite sides of the side wall 110 for complementary slide locking with corresponding tabs (or slots) on the cover 102.

Figure 4:
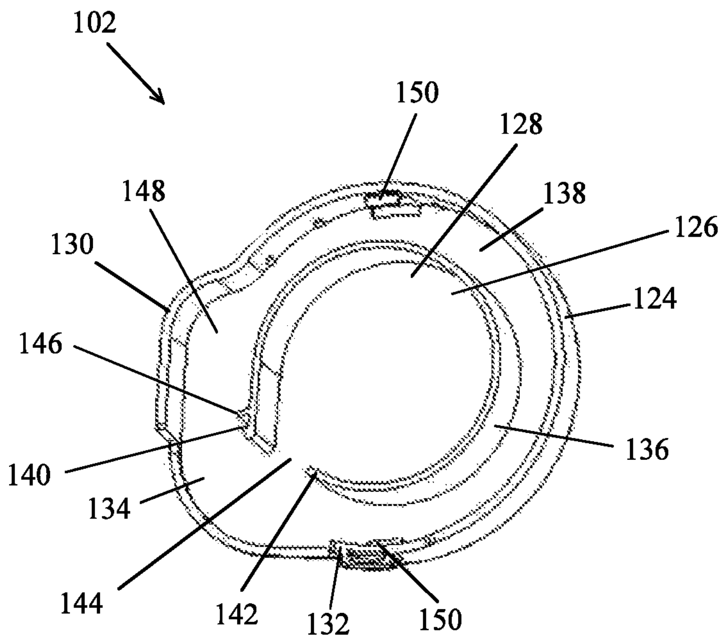
FIG. 4 shows a rear view of the embodiment of the cover of FIG. 2.

Turning to the cover 102, with reference to FIG. 4 showing a rear view of it, the cover 102 has a side wall 124 and an inner surface 126 facing towards the inner surface (see FIG. 3 at 112) of the body (see FIG. 3 at 104) when it is engaged with the body (see FIG. 3 at 104) to form the noise reduction device (see FIG. 2 at 100). The side wall 124 extends perpendicularly from the periphery of the inner surface 126 and partially surrounds the cover 102 to form a cavity 128. In this embodiment, the cavity 128 is open with the side wall 124 configured substantially as a C-shape to define a second end portion 130 and a third end portion 132 on the side wall 124 respectively, leaving an open portion 134.

The cover 102 has a guiding member 136 being configured to extend substantially perpendicularly from the inner surface 126. The guiding member 136 itself defines at least a part of a gas passage 138, and is configured in a way to form the gas passage 138 between the body (see FIG. 3 at 104) and the cover 102 when they are engaged together. One skilled in the art would appreciate that possible configurations of the guiding member such as a spiral including Cotes's spiral, Archimedean spiral and golden spiral, may be used depending on the desired design and noise reduction requirements.

Preferably, the area enclosed by the guiding member 136 is at least twice than area of the gas outlet 106 in order to increase the effective filtering area of the filter 115 and reduce gas resistance, thereby further reducing noise production.

In this embodiment, the guiding member 136 is substantially in form of a C-shape. The guiding member 136 has a fourth end portion 140 and a fifth end portion 142 defining an opening 144 aligning with the open portion 134 and to be closed by the side wall 110 of the body (see FIG. 3 at 104) when the body (see FIG. 3 at 104) and the cover 102 are engaged. The fourth end portion 140 includes a projection 146 for additional engagement and position fixing with the first end portion 111 of the body 104 (see FIG. 3 at 111) when the body 104 and the cover 102 are engaged together.

The fourth end portion 140 and the second end portion 130 together define a flow deflecting portion 148 being a part of the gas passage 138 to provide an enlarged section for an increased level of gas entry, and facilitate a spiral flow of the gas into the gas passage. The flow deflecting portion 148 may also avoid transmission of noise from the blower inside the respiratory apparatus to the outside environment.

In this embodiment, the cover 102 is detachably engageable with the body (see FIG. 3 at 104) and preferably encloses the body 104 after engagement. Similar to the body 104, two tabs 150 may be respectively arranged on substantially diametrically opposite sides of the side wall 124 for complementary slide locking with corresponding slots 122 on the body 104 to form a bayonet mount.

Figure 5:
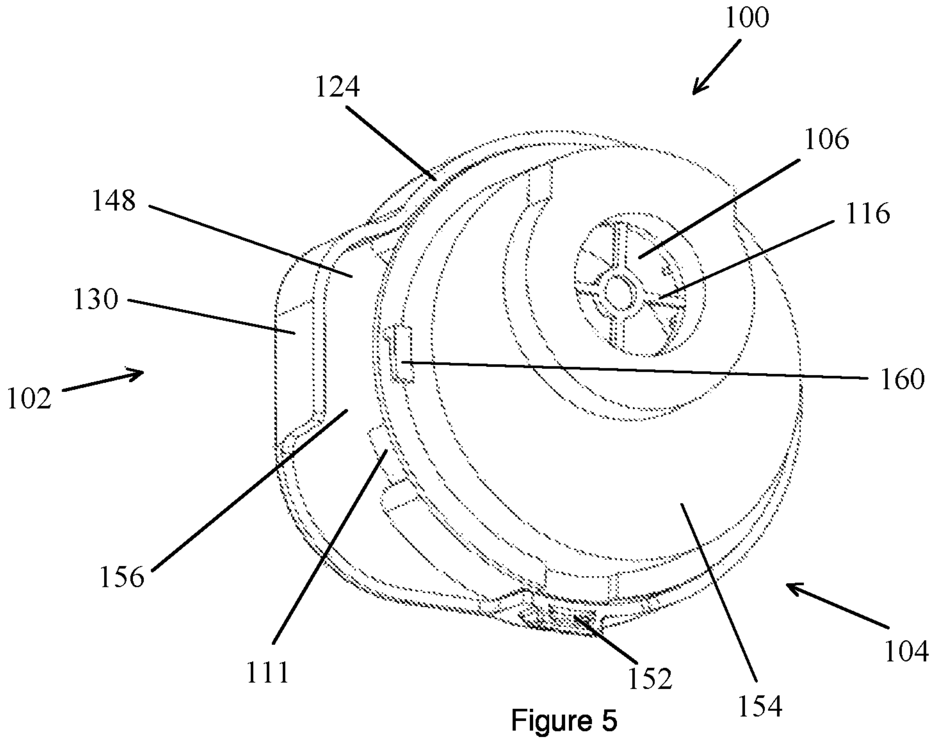
FIG. 5 shows an embodiment of the noise reduction device when the body and the cover are engaged.

FIG. 5 shows the noise reduction device 100 when the body 104 and the cover 102 are slidably locked to one another. In this embodiment, the body 104 is oriented and inserted into the cavity (see FIG. 4 at 128) of the cover 102 with the tabs (see FIG. 4 at 150) being received in the slots (see FIG. 3 at 122). A slight turning of either the body 104 or the cover 102 locks the two components with a bayonet lock as a locking mechanism 152 to hold them in place. In the present invention, the locking mechanism 152 includes at least one slot (see FIG. 3 at 122) arranged on the body 104, and at least one corresponding tab (see FIG. 4 at 150) arranged on the cover 102. In another embodiment, the locking mechanism 152 may include a pair of magnetic members arranged on the cover 102 and the body 104 as the locking means. One skilled in the art would appreciate that other locking means, such as a push lock, a slide lock, a screw, a plug and/or a combination thereof, may be used herein.

In this figure, the outer surface 154 of the body 104 shows the gas outlet 106 which is to be mounted to a respiratory apparatus (see FIG. 7 at 162) for discharge of a gas into the respiratory apparatus. The flow deflecting portion 148, which is not covered by the body 104, is shown adjacent to the second end portion 130 of the side wall 124. Adjacent to the flow deflecting portion 148 is a gas inlet 156 arranged between the side wall (see FIG. 3 at 110) and the side wall 124. The first end portion 111 of the side wall 110 is arranged adjacent to the gas inlet 156. Two tabs 160 (only one is shown) are disposed on substantially diametrically opposite ends of the outer surface 154 for detachable mounting on the respiratory apparatus (see FIG. 7 at 162) through sliding. One skilled in the art would appreciate that other locking means such as screwing may also be used depending on the configuration of the respiratory apparatus.

Figure 6:
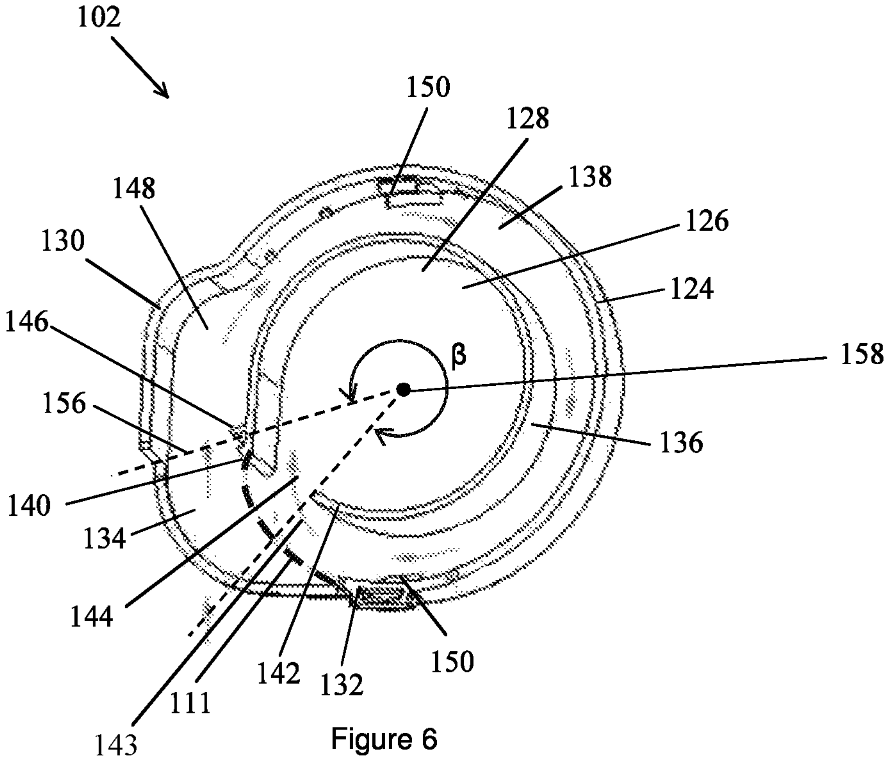
FIG. 6 shows the direction of the gas flow in an embodiment of the noise reduction device when the body is engaged with the cover.

Referring to FIG. 6, when the body (see FIG. 2 at 104) and the cover 102 are engaged, the side wall 110 of the body (see FIG. 2 at 104) is received in the gas passage 138 and the body (see FIG. 2 at 104) is enclosed by the cover 102. The location of the first end portion (see FIG. 3 at 111) is shown as a dotted line forming a seal with the projection 146 and abutting the fourth end portion 140 of the guiding member 136 to define the planar spiral gas passage 138 between the side wall 110 and the guiding member 136, wherein the fifth end portion 142 spaces apart from the side wall (see FIG. 3 at 110) to form a gap 143 and the gas inlet 156 is arranged to be perpendicularly to the gas outlet 106 in this embodiment. In an embodiment where a filter (see FIG. 3 at 115) is placed in the body (see FIG. 3 at 104), the guiding member 136 is in contact with the filter (see FIG. 3 at 115) when the body (see FIG. 3 at 104) and the cover 102 are engaged so as to keep the filter (see FIG. 3 at 115) in place by sandwiching the filter (see FIG. 3 at 115) between the guiding member 136 and the body (see FIG. 2 at 104). This also helps to avoid oscillation of the filter (see FIG. 3 at 115) between the body (see FIG. 3 at 104) and the cover 102 when the gas passes the filter (see FIG. 3 at 115).

During operation, a gas, typically atmospheric air, is drawn to the gas inlet 156 preferably by a blower of the respiratory apparatus, where the gas travels from the flow deflecting portion 148 of a wider cross section to the gas passage 138 of a narrower cross section for a smoother gas flow by maintaining or even reducing gas resistance. The gas then flows through the gas passage 138, the gap 143, and to the opening 144. The gas then passes through the filter (see FIG. 3 at 115) which is in contact with the guiding member 136 when the body (see FIG. 3 at 104) and the cover 102 are engaged, and finally reaches the gas outlet (see FIG. 3 at 106) (shown by arrows). One skilled in the art would appreciate that with such configuration, the incoming gas is forced to travel an angular rotation 13 about a centre 158 of the gas outlet (see FIG. 3 at 106) of at least 330 degrees from the gas inlet 156 to the gas outlet 106, which is over 2.5 times longer than the gas passage 3 described in FIG. 1 without substantive increment in size of the noise reduction device 100. In an alternative embodiment, the gas passage 138 formed may direct the gas flow to travel an angular rotation 13 about the centre 158 of the gas outlet (see FIG. 3 at 106) of at least 180 degrees, at least 270 degrees or at least 300 degrees, relative to the gas inlet 156 before discharging at the gas outlet (see FIG. 3 at 106).

Figure 7:
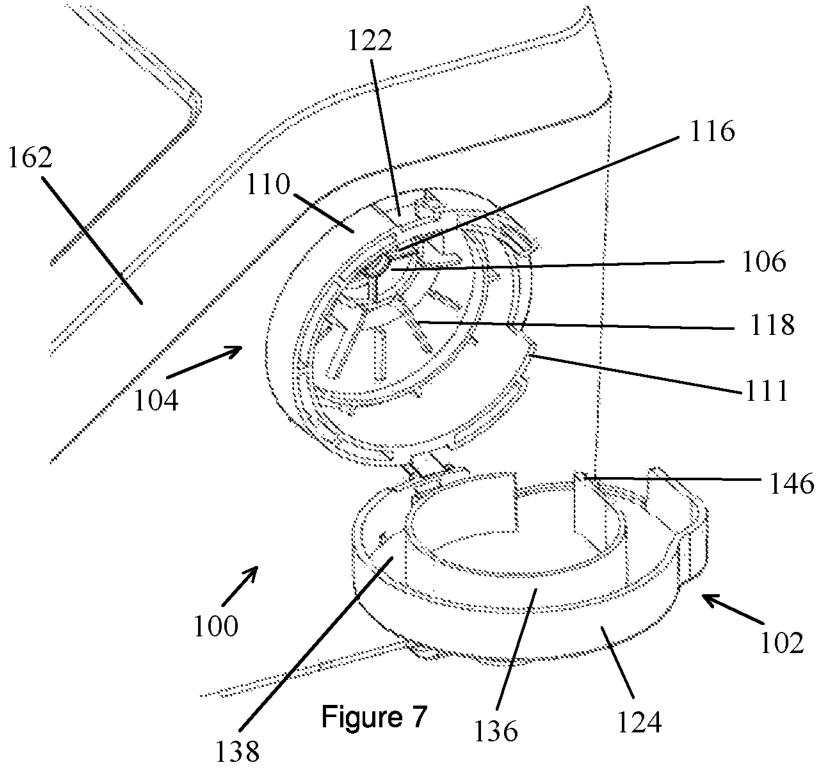
FIG. 7 shows an embodiment of the noise reduction device being mounted to a respiratory apparatus.

FIG. 7 shows the noise reduction device 100 of the present invention being mounted to a respiratory apparatus 162. The body 104 is mounted to one side of the respiratory apparatus 162 by the tabs 160 (see FIG. 5 at 160). The tabs 150 (see FIG. 4 at 150) on the cover 102 are oriented to be slidably locked with the corresponding slots 122. A seal is to be formed by the first end portion 111 and the projection 146 of the guiding member 136 to define the gas passage 138.

Figure 8:
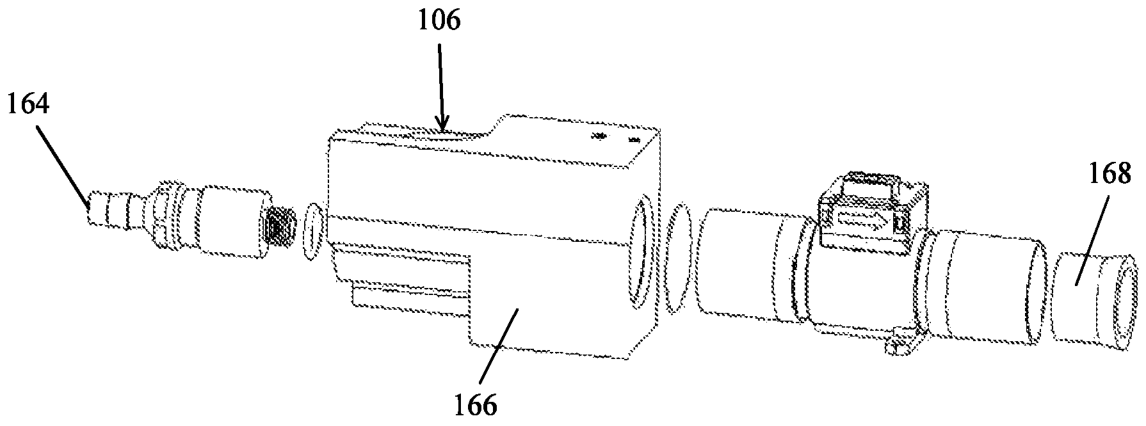
FIG. 8 shows an embodiment of the components of the respiratory apparatus in FIG. 7.

Referring to FIG. 8 which shows an embodiment of the components of the respiratory apparatus (see FIG. 7 at 162), it may further include a pressurized gas inlet 164 for supplying a pressurized gas, a chamber 166 in fluid communication with the gas outlet 106 (see FIG. 7 at 106) of the noise reduction device (see FIG. 5 at 100) and the pressurized gas inlet 164 wherein the chamber 166 is for mixing atmospheric air and the pressurized gas, and a noise-damping device 168 disposed downstream of the chamber 166. The noise-damping device 168 is made of a porous material, for example, porous ceramic, porous plastics or porous polymeric foams, for absorbing noise in order to further minimize the noise generated when supplying a gas source to the respiratory apparatus.

It is believed that the noise reduction device 100 in the present invention can provide obvious noise reduction effect by decreasing the turbulence and resistance of gas flow to a larger extent and thus reducing the noise caused by the friction between the fluctuated gas flow and the gas inlet of the respiratory apparatus. Moreover, the configuration of the guiding member 136 being located on the cover 102 provides an easier and more convenient way to clean the gas passage 138. The cover 102 can be disengaged from the body 104 and subject to common sterilization methods of medical equipment. Such arrangement also facilitates replacement of the cover 102 in case abrasion or damage is found on the guiding member 136 which may increase turbulent flow of the incoming gas and thus causes noise.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

The invention claimed is:

1. A noise reduction device for a respiratory apparatus, comprising:

a body configured to be mounted on the respiratory apparatus, the body comprising a side wall and a gas outlet supported by a supporting structure, the supporting structure having a plurality of upright protrusions on an inner surface of the body connecting to the gas outlet; and a cover configured to be detachably engageable with the body for forming a gas inlet and a gas passage, the cover comprising a guiding member defining at least a part of the gas passage, wherein the guiding member is configured to be coupled with the side wall of the body to form the gas passage between the body and the cover; and wherein the body is arranged to house a filter therein, the plurality of upright protrusions on the inner surface of the body being configured to support the filter, and the filter is sandwiched between the guiding member and the plurality of upright protrusions provided on the inner surface of the body.

2. The noise reduction device of claim 1, wherein the gas passage formed directs a flow of gas to an angular rotation about a centre of the gas outlet of at least 180 degrees to 330 degrees relative to the gas inlet before discharging at the gas outlet.

3. The noise reduction device of claim 1, wherein the gas passage formed directs a flow of gas to an angular rotation about a centre of the gas outlet of at least 270 degrees to 330 degrees relative to the gas inlet before discharging at the gas outlet.

4. The noise reduction device of claim 1, wherein the gas passage formed directs a flow of gas to an angular rotation about a centre of the gas outlet of at least 330 degrees relative to the gas inlet before discharging at the gas outlet.

5. The noise reduction device of claim 1, wherein the guiding member is configured to extend perpendicularly from an inner surface of the cover towards the body.

6. The noise reduction device of claim 5, wherein the guiding member is in form of a C-shape.

7. The noise reduction device of claim 6, wherein the guiding member comprises an end portion forming a seal with a side wall of the body.

8. The noise reduction device of claim 1, wherein a portion of the gas inlet is formed between the side wall of the body and a side wall of the cover.

9. The noise reduction device of claim 8, wherein a portion of the gas inlet is formed between the side wall of the cover and the guiding member.

10. The noise reduction device of claim 1, wherein the cover has a flow deflecting portion adjacent to the gas inlet.

11. The noise reduction device of claim 1, wherein an area enclosed by the guiding member is at least twice than an area of the gas outlet.

12. The noise reduction device according to claim 1, further comprises a locking mechanism for slidably locking the cover to the body.

13. The noise reduction device of claim 12, wherein the locking mechanism comprises at least one slot arranged on the body, and at least one corresponding tab arranged on the cover.

14. The noise reduction device of claim 1, wherein the gas inlet is arranged perpendicularly to the gas outlet.

15. The noise reduction device of claim 1, wherein the gas inlet is arranged for supplying atmospheric air to the respiratory apparatus.

16. A respiratory apparatus comprising a noise reduction device, wherein the noise reduction device comprises:

a body configured to be mounted on the respiratory apparatus, the body comprising a side wall and a gas outlet supported by a supporting structure, the supporting structure having a plurality of upright protrusions on an inner surface of the body connecting to the gas outlet; and a cover configured to be detachably engageable with the body for forming a gas inlet and a gas passage, the cover comprising a guiding member defining at least a part of the gas passage, wherein the guiding member is configured to be coupled with the side wall of the body to form the gas passage between the body and the cover; and wherein the body is arranged to house a filter therein, the plurality of upright protrusions on the inner surface of the body being configured to support the filter, and the filter is sandwiched between the guiding member and the plurality of upright protrusions provided on the inner surface of the body.

17. The respiratory apparatus of claim 16, further comprising: a pressurized gas inlet for supplying a pressurized gas; a chamber in fluid communication with the gas outlet of the noise reduction device and the pressurized gas inlet, the chamber for mixing atmospheric air and the pressurized gas; and a noise-damping device disposed downstream of the chamber.

* * * * *